(12) United States Patent
Leyde

(10) Patent No.: US 6,266,562 B1
(45) Date of Patent: Jul. 24, 2001

(54) DEFIBRILLATOR WITH AUTOMATED TEST LOAD

(75) Inventor: Kent W. Leyde, Redmond, WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/302,558

(22) Filed: Apr. 30, 1999

(51) Int. Cl.[7] .................................................. A61N 1/36
(52) U.S. Cl. ............................................................ 607/5
(58) Field of Search ................................ 607/5, 6, 7, 8

(56) References Cited

U.S. PATENT DOCUMENTS

| | | | |
|---|---|---|---|
| 4,628,935 | * 12/1986 | Jones et al. ................................ | 607/5 |
| 5,230,336 | 7/1993 | Fain et al. .................................. | 607/7 |
| 5,249,573 | 10/1993 | Fincke et al. . | |
| 5,591,213 | 1/1997 | Morgan ...................................... | 607/5 |
| 5,601,612 | 2/1997 | Gliner et al. ............................... | 607/7 |
| 5,607,454 | 3/1997 | Cameron et al. .......................... | 607/5 |
| 5,611,815 | 3/1997 | Cole et al. ................................. | 607/5 |
| 5,617,853 | 4/1997 | Morgan .................................. | 128/640 |
| 5,662,690 | 9/1997 | Cole et al. ................................. | 607/5 |
| 5,749,904 | 5/1998 | Gliner et al. ............................... | 607/7 |
| 5,749,905 | 5/1998 | Gliner et al. ............................... | 607/7 |
| 5,797,969 | 8/1998 | Olson et al. . | |

* cited by examiner

Primary Examiner—Scott M. Getzow

(57) ABSTRACT

A defibrillator is provided with a test load feature which is automatically inserted into electrode paddle jacks when a defibrillator housing lid is closed, placing the defibrillator controller into a TEST MODE. Closing the lid permits actual firing of a shock pulse through the electrode connector through the test load, opening the lid automatically disconnects the test load and permits insertion of electrode paddles, placing the defibrillator into a PATIENT-READY MODE.

8 Claims, 5 Drawing Sheets

DEFIBRILLATOR WITH AUTOMATED TEST LOAD

BACKGROUND OF THE INVENTION

1. Field of the Invention

The invention relates generally to defibrillators and, more specifically, to an external defibrillator having a built-in test load feature.

2. Description of Related Art

Defibrillators are used to apply an electrical shock to a patient's heart in response to a life-threatening condition such as an arrhythmia or cardiac arrest. External, or transthoracic, defibrillators deliver a pulse through a pair of electrodes placed on the patient's chest or back by the attending medical personnel. As shown in FIG. 1 (Prior Art), a defibrillator 101 generally includes a controller 103 (such as a microprocessor) which controls the operation of an energy source 105, 107, 109 and an energy discharge switch 111 to deliver an electrical pulse to electrodes 113, 115 (sometimes referred to in the art as the "paddles"). The controller 103 receives a command through a user interface, "shock button," 117. The electrodes 115 are also used to provide patient-feedback 119, 121 to the controller 103. Defibrillator operational readiness and patient-related information may be monitored on a display 121. Particularly in portable defibrillators, the electrodes 115 are disposable, typically packaged having a conductive gel on the paddle faces to lower the electrical resistance between the electrodes and the patient 131 and an adhesive for holding the electrode paddles on the patient. Therefore, the paddles 115 are releasably attached to the defibrillator 101 via an electrode connector, or connector port, 113.

Before actual use of a defibrillator 101 where the patient 131 provides the load across the paddles 115, it is important, particularly in an emergency situation, for medical personnel to know that the defibrillator is fully functional. A variety of defibrillator test methods and apparatus have been developed. Separate test simulation units which plug into the electrode connector to simulate a patient feedback are used in defibrillator training. In U.S. Pat. Nos. 5,591,213 and 5,617,853 by Morgan, assigned to the common assignee of the present invention, patient simulation and analyzer circuits are built into a defibrillator. Neither provides the capability of testing through the actual electrode port itself, therefore leaving a critical component untested as to operability. In U.S. Pat. Nos. 5,611,815 and 5,662,690 by Cole et al., assigned to the common assignee of the present invention, such training mode circuitry simulates delivery of a shock without actually delivering the pulse to the electrodes. U.S. Pat. Nos. 5,645,571 and 5,797,969, assigned to SurVivaLink Corp., show built-in self-test systems; again, neither provides a capability of testing through the actual electrode port itself.

There is a need for a test load implementation scheme which automatically is activated when the defibrillator unit is not in use with a patient and which tests the ability of the unit actually to deliver a shock pulse through the electrode connector.

SUMMARY OF THE INVENTION

In its basic aspects, the present invention provides a defibrillator system including: an external defibrillator apparatus, including an electrode connector for connecting electrode paddles to the apparatus; and a test load mounted on the defibrillator apparatus such that the test load is selectively coupled to the electrode connector or selectively decoupled from the electrode connector such that the electrode connector is cleared for connecting the electrode paddles thereto.

In another basic aspect, the present invention provides a test load device for a defibrillator apparatus having a port for connecting electrodes thereto, including: a load for receiving a shock pulse from the apparatus; coupled to the load, a connector device for electrically connecting the load means to the port; and mounting for the load means for automatically inserting the connector into the port when the apparatus is not in use. In another embodiment, a basic aspect of the present invention includes a mechanism for providing a stimulus function to the defibrillator apparatus.

In another basic aspect, the present invention provides a method for putting a defibrillator apparatus into a test mode. The method includes the steps of:

providing a lid that covers a defibrillator apparatus' electrode port;

providing the lid with test load device that inserts into the electrode port upon closing the lid;

closing the lid such that the test load device is electrically connected to the electrode connector;

when the lid is closed, providing a signal to a defibrillator controller indicative that the test load device is connected to the electrode connector; and instituting a test mode based on the signal.

It is an advantage of the present invention that it eliminates the need for use of separate patient simulation test units.

It is another advantage of the present invention that allows a closed loop test through electrode connectors of the defibrillator.

It is another advantage of the present invention that it allows automatic wake-up self test operation to be incorporated into a defibrillator which tests all functions of the defibrillator.

It is another advantage of the present invention that it prevents inadvertent contact with the electrode connector during self test mode operation of the defibrillator, thereby providing a safety feature.

Other objects, features and advantages of the present invention will become apparent upon consideration of the following explanation and the accompanying drawings, in which like reference designations represent like features throughout the drawings.

The drawings referred to in this specification should be understood as not being drawn to scale except if specifically noted.

DESCRIPTION OF THE PREFERRED EMBODIMENT

Reference is made now in detail to a specific embodiment of the present invention, which illustrates the best mode presently contemplated by the inventor for practicing the invention. Alternative embodiments are also briefly described as applicable.

Figure 2A:
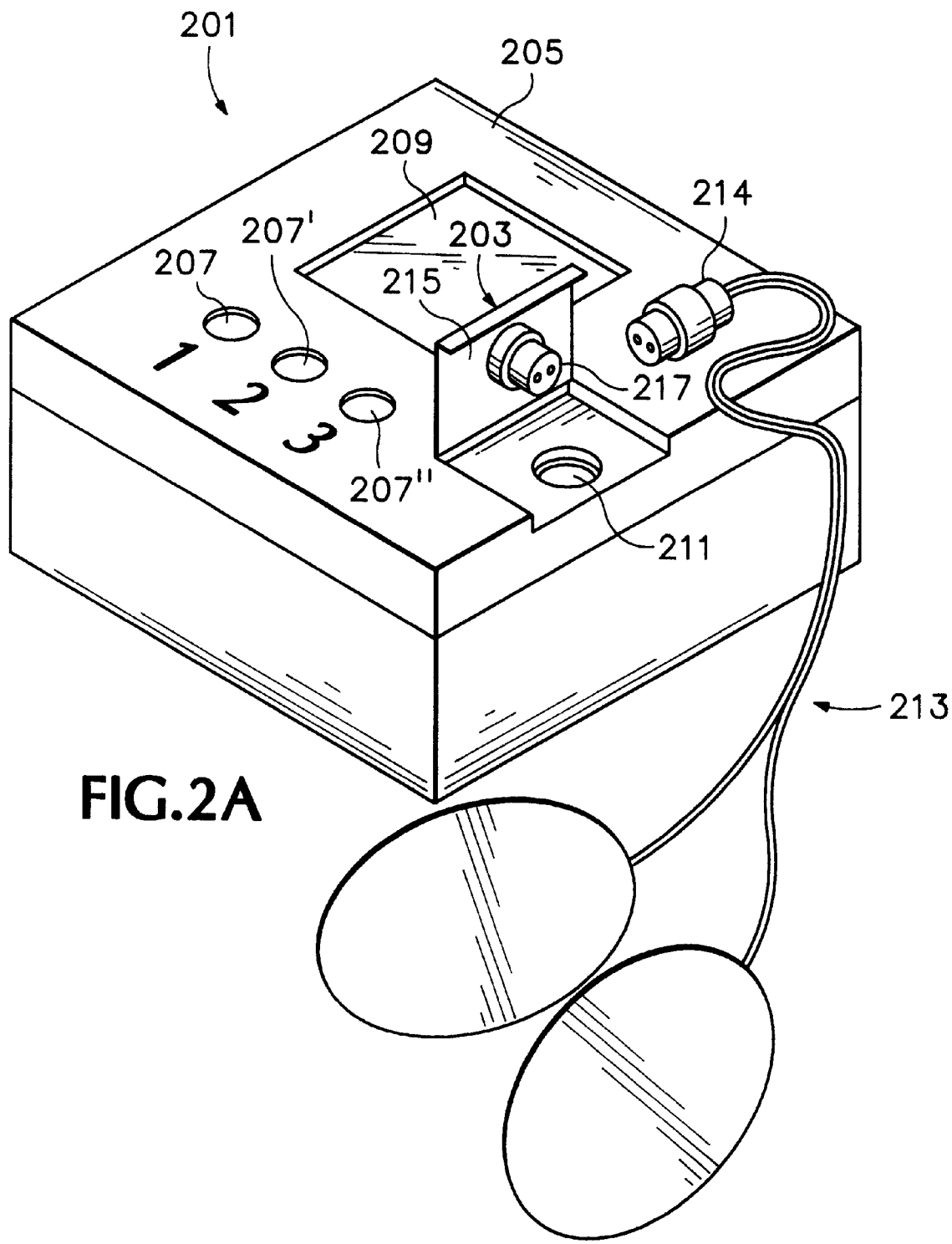
FIG. 2A is a perspective drawing d a first embodiment of a defibrillator in accordance with the present invention.
Figure 2B:
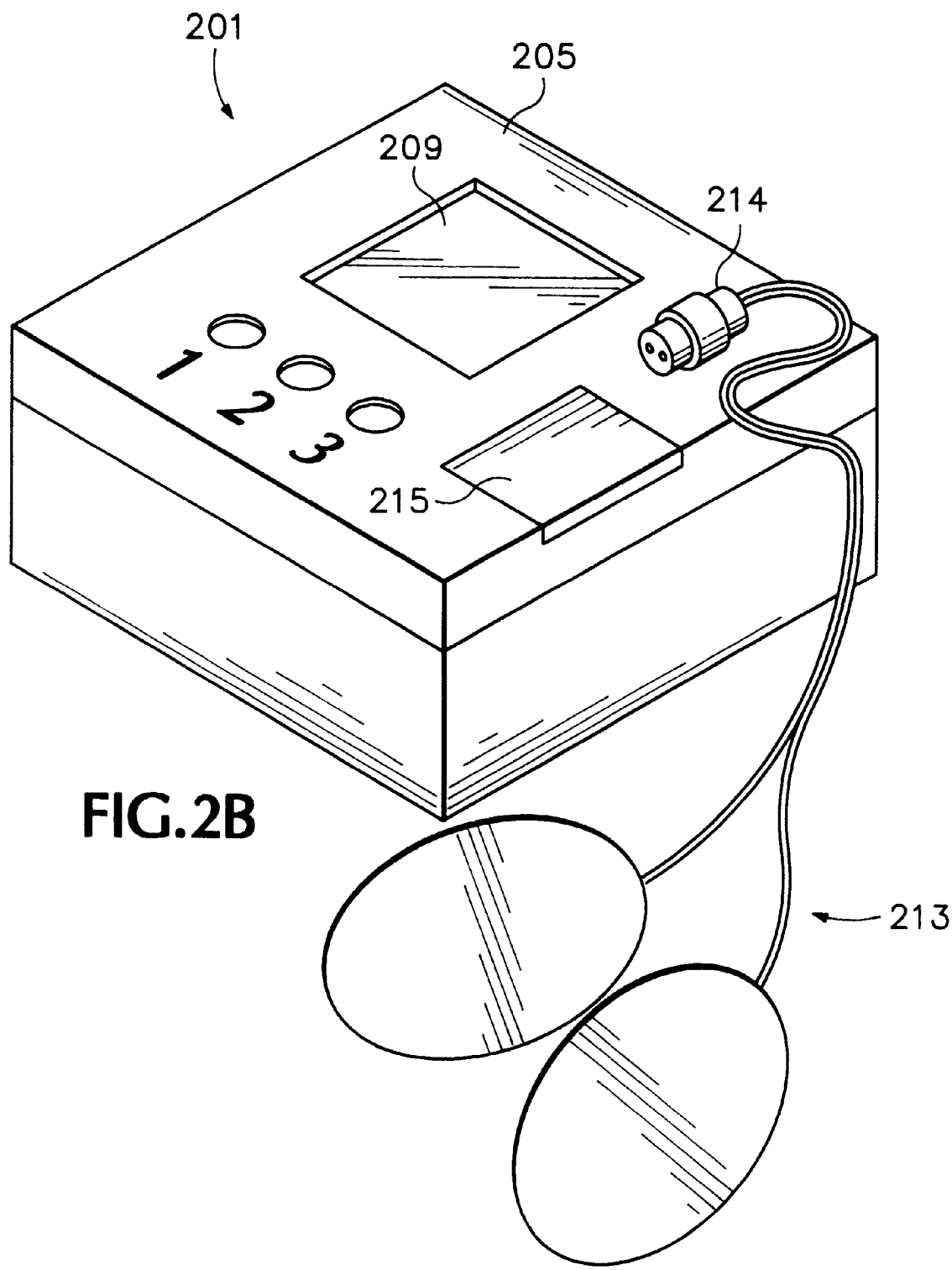
FIG. 2B is the perspective drawing of FIG. 2B with the defibrillator in a test mode configuration.
Figure 3:
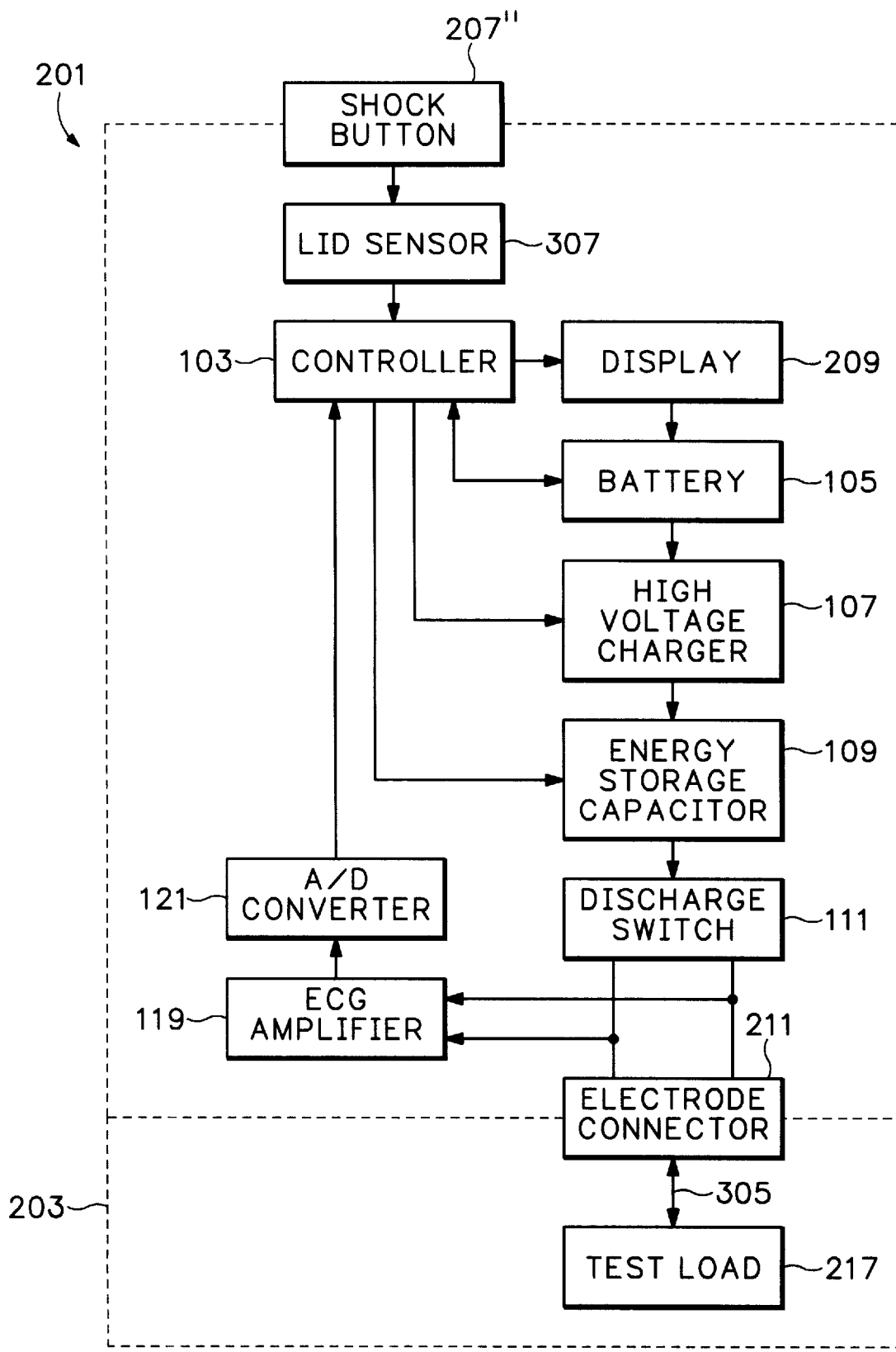
FIG. 3 is a block diagram of a defibrillator as shown in FIG. 2.
Figure 4A:
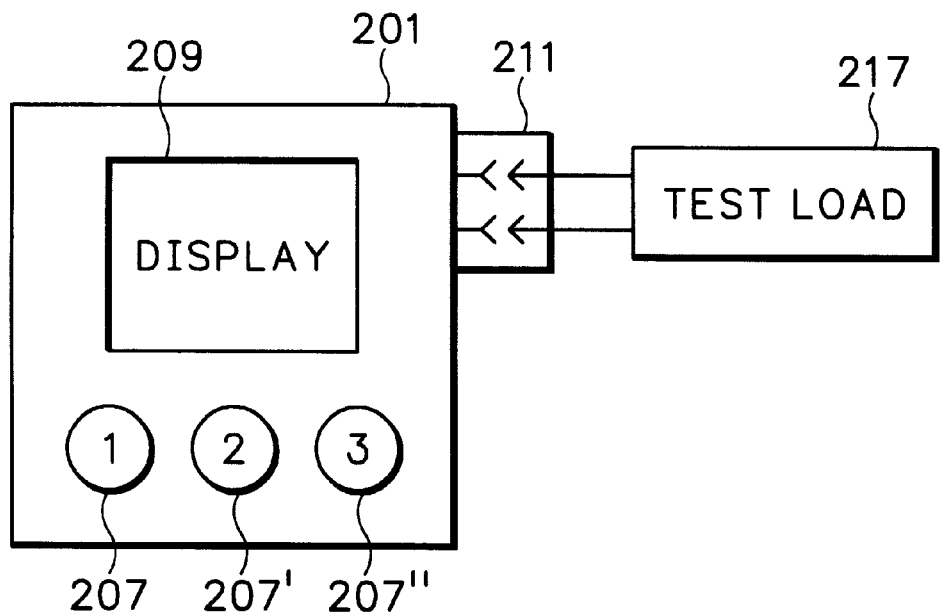
FIG. 4A is a first embodiment of a test load device in accordance with the present invention as used in accordance with FIGS. 2 and 3.
Figure 4B:
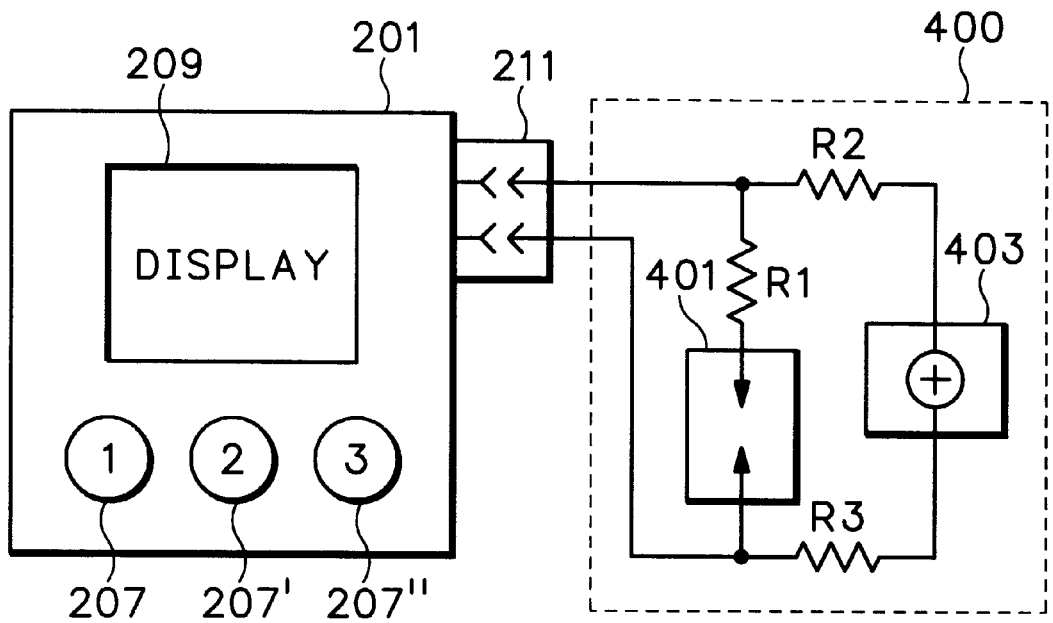
FIG. 4B is a second embodiment of a test load device in accordance with the present invention as used in accordance with FIGS. 2 and 3 and 4A.

FIGS. 2A and 2B depict an external defibrillator 201 having an automated test load feature 203 in accordance with the present invention. The defibrillator housing 205 contains the operative components as shown in FIGS. 3, 4A and 4B, explained hereinafter. Three standard operating buttons 207, 207', 207" (labeled "1," "2," and "3" in accordance with common industry convention) and an operator display 209 are provided in accordance with known state-of-the-art technology. In this embodiment, an electrode paddle jack port 211 for a removable electrode set 213, having an electrical connector plug 214, compatible with the jack port 211. The test load feature 203 includes a housing lid 215 that is rotatably mounted in any suitable design specific manner to the housing 205. A test load 217 (see also FIGS. 4A and 4B) is mounted within the lid 215 such that upon closing the lid, the test load automatically is inserted into the electrode paddle jack port 211 and electrically connected thereto.

With the test load 217 automatically inserted in the jack port 211 by closing the lid 215 as shown in FIG. 2B, the defibrillator 201 controller 103 (see FIG. 3) programs can perform tests and diagnostics which use the actual electrode set 213 paddle jack port 211 connector. Thus, for example, a defibrillator 201 on the shelf can do a self test every thirty minutes and issue a warning signal if a failure occurs. A variety of test modes can be programmed in accordance with the needs of a specific implementation of the defibrillator 201.

Upon opening the lid 215, the test load 217 is withdrawn from the jack port 211. If an electrode set 213 is inserted in the jack port 211 when no self test warnings have issued and a failure or not ready indication is displayed 209, there is a high confidence that the problem is in the electrode set 213 rather than the defibrillator 201 itself. A replacement electrode set can be rapidly selected and substituted for the faulty one.

Figure 1:
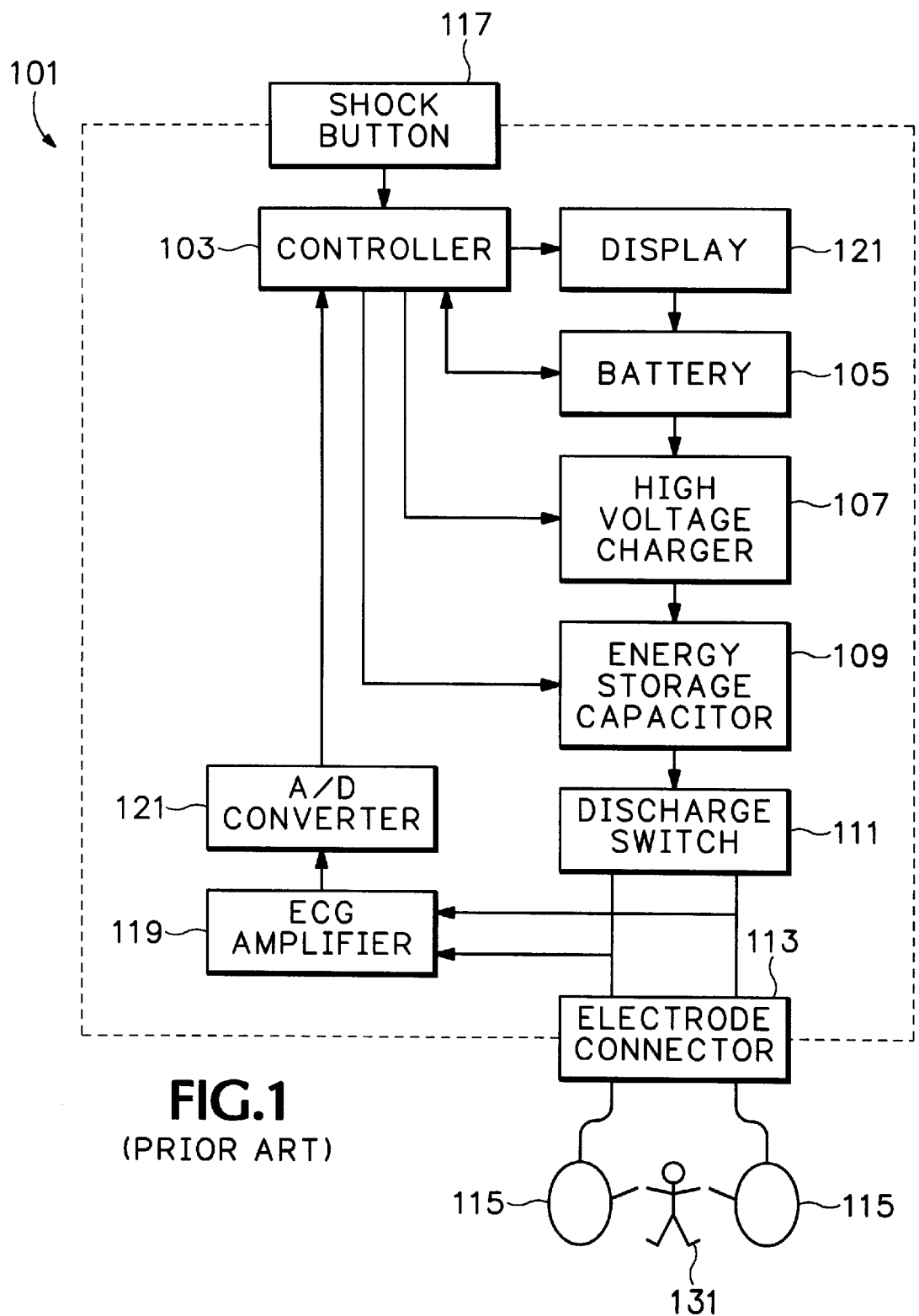
FIG. 1 (PRIOR ART) is a block diagram of a defibrillator.

FIG. 3 is a schematic block diagram for the defibrillator 201. In comparison with FIG. 1 (Prior Art), the permanent, automated, test load 217 is added, configured to be automatically electrically connected (arrow 305) to the electrode connector 113 whenever the defibrillator 201 is not in use with a patient upon closing the lid 215 (FIG. 2 only). In combination with a lid sensor 307 connected to the controller 103 to signal active coupling-decoupling of the test load 217 to the electrode connector 211, the defibrillator 201 is automatically configured in a TEST MODE or a PATIENT-READY MODE, respectively, when the lid is closed or opened.

FIGS. 4A and 4B show two exemplary embodiments for the test load feature, analogous to element 217, FIG. 3. Two functions are of significance to the defibrillator user; therapy (viz., inducing a shock across the patient's heart, a stimulus function) and diagnostics, i.e., electrocardiogram ("ECG") information from the patient, a response function. Both go through the same connector 211. In a simple test load embodiment as depicted in FIG. 4A, the test load 217 would comprise, for example, a standard therapy load in defibrillators of approximately fifty ohms. Thus, the test load 217 allows an actual firing of a full energy shock using the front panel shock button 207", or automatically when the unit is in a self test mode, whenever the test load 217 is connected to the paddle electrode connector 211 as indicated by the lid sensor 307 to the controller 103. Any test success or failure is shown on the display 209.

FIG. 4B shows a more detailed test load 400 which incorporates a more sophisticated scheme in which an ECG simulated signal generator 403 provides patient simulation signals (in the millivolt range) as responses that are used to test other controller 103 (FIG. 3) functions—for example, patient feedback analyzer and waveform display and chart recording tests—as would be known in the state of the art (see e.g., Morgan, supra, incorporated herein by reference). The test load 400 includes a commercial spark gap device 401 connected in parallel with a resistor R1. Protection resistors R2 and R3 and the ECG signal generator 403 are shunted by R1 and the spark gap device 401 from the defibrillation therapy pulse (in the 2000 volt range).

In operation, with a test load 217/400 automatically inserted in the electrode connector 211, the defibrillator controller 103 can be programmed to perform diagnostics without user input. Thus, for example, a defibrillator on the shelf can do a self test every thirty minutes and issue a warning signal if a failure occurs, e.g., low battery 105 power.

The foregoing description of the preferred embodiment of the present invention has been presented for purposes of illustration and description. It is not intended to be exhaustive or to limit the invention to the precise form or to exemplary embodiments disclosed. Obviously, many modifications and variations will be apparent to practitioners skilled in this art. Similarly, any process steps described might be interchangeable with other steps in order to achieve the same result. The embodiment was chosen and described in order to best explain the principles of the invention and its best mode practical application, thereby to enable others skilled in the art to understand the invention for various embodiments and with various modifications as are suited to the particular use or implementation contemplated. It is intended that the scope of the invention be defined by the claims appended hereto and their equivalents.

What is claimed is:

1. A defibrillator system comprising:
   an external defibrillator apparatus, including an electrode connector for connecting electrode paddles to the apparatus; and
   a test load mounted on the defibrillator apparatus such that the test load is selectively coupled to the electrode connector or selectively decoupled from the electrode connector such that the electrode connector is cleared for connecting the electrode paddles thereto.

2. The system as set forth in claim 1, comprising:
   the test load is mounted on a lid wherein closing the lid electrically connects the test load to the electrode connector and opening the lid electrically disconnects the test load from the electrode connector.

3. The system as set forth in claim 2, comprising:
   means for indicating the apparatus is in a test mode when the lid is closed and a patient-ready mode when the lid is open.

4. The system as set forth in claim 1, comprising:
   the test load is configured for allowing actual shock pulse delivery through the electrode connector.

5. The system as set forth in claim 3, comprising:
   the test load including means for delivering simulated patient electrocardiogram feedback to the apparatus through the electrode connector.

6. A test load device for a defibrillator apparatus having a port for connecting electrodes thereto, comprising:

load means for receiving a shock pulse from the apparatus;

coupled to the load means, connector means for electrically connecting the load means to the port; and mount means for mounting the load means to the apparatus and for automatically inserting the connector means into the port when the apparatus is not in use.

7. The device as set forth in claim 6, comprising:

the load means includes means for providing a stimulus function to the apparatus.

8. A method for putting a defibrillator apparatus into a test mode, comprising the steps of:

providing a lid that covers a defibrillator apparatus' electrode port;

providing the lid with test load device that inserts into the electrode port upon closing the lid;

closing the lid such that the test load device is electrically connected to the electrode connector;

when the lid is closed, providing a signal to a defibrillator controller indicative that the test load device is connected to the electrode connector; and instituting a test mode based on the signal.

* * * * *